United States Patent
Fujinami

(10) Patent No.: US 8,299,245 B2
(45) Date of Patent: *Oct. 30, 2012

(54) METHOD FOR PRODUCING PYRIMIDINE COMPOUND

(75) Inventor: Michihiko Fujinami, Misawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 887 days.

This patent is subject to a terminal disclaimer.

(21) Appl. No.: 12/297,119

(22) PCT Filed: Apr. 23, 2007

(86) PCT No.: PCT/JP2007/059277
§ 371 (c)(1),
(2), (4) Date: Nov. 3, 2008

(87) PCT Pub. No.: WO2007/123277
PCT Pub. Date: Nov. 1, 2007

(65) Prior Publication Data
US 2009/0111984 A1 Apr. 30, 2009

(30) Foreign Application Priority Data

Apr. 24, 2006 (JP) ................. 2006-118803
Oct. 2, 2006 (JP) ................. 2006-270442

(51) Int. Cl.
C07D 403/04 (2006.01)
C07D 401/04 (2006.01)
A01N 43/54 (2006.01)
(52) U.S. Cl. ....................... 544/319; 544/328
(58) Field of Classification Search .................. 544/319, 544/328
See application file for complete search history.

(56) References Cited

U.S. PATENT DOCUMENTS

| | | | |
|---|---|---|---|
| 5,011,927 A | 4/1991 | Hamprecht | |
| 5,093,482 A | 3/1992 | Schudehutte et al. | |
| 5,587,465 A | 12/1996 | Schundehutte et al. | |
| 5,668,140 A | 9/1997 | Schaper et al. | |
| 6,838,463 B2 * | 1/2005 | Mizuno et al. ................ | 514/269 |
| 2003/0092723 A1 | 5/2003 | Weintritt et al. | |
| 2006/0199800 A1 | 9/2006 | Mizuno et al. | |
| 2007/0035986 A1 | 2/2007 | Houston | |
| 2008/0039445 A1 * | 2/2008 | Mizuno ................... | 514/217.06 |

FOREIGN PATENT DOCUMENTS

| | | |
|---|---|---|
| JP | 2-225473 A | 9/1990 |
| JP | 6-234750 A | 8/1994 |
| JP | 2003-528862 A | 9/2003 |
| JP | 2005-350353 A | 12/2005 |
| WO | 2004/099160 A1 | 11/2004 |
| WO | 2006/051891 A1 | 5/2006 |

OTHER PUBLICATIONS

Zhurnal Organicheskoi Khimii, vol. 25, No. 8, Aug. 1989, pp. 1780-1783.
D. Ranganathan et al., "The Demonstration of Norman O +N Claisen Rearrangement in Purines", Tetrahedron, vol. 42, No. 17, 1986, pp. 4873-4878.
B.G. Szczepankiewicz et al., "Synthesis of Purines and Other Fused Imidazoles from Acyclic Amides and Guanidines", Organic Letters, vol. 7, No. 9, 2005, pp. 1833-1835.
M. Makosza and S. Ostrowski, "Reactions of Chlorinated Pyrimidine Derivatives with Carbanions Bearing Nucleophugal Groups at the Carbanionic Center", Polish. J. Chem., vol. 74, 2000, pp. 1355-1361.
Tumkevicius, S. et al., Synthesis of N-Aryl-2-amino-4-oxo-3, 4-dihydrothieno[2, 3-] pyrimidine-6-carboxamides, Journal of Heterocyclic Chemistry, vol. 42, No. 7, (2005), pp. 1305-1310.

* cited by examiner

*Primary Examiner* — Venkataraman Balasubramanian
(74) *Attorney, Agent, or Firm* — Sughrue Mion, PLLC

(57) ABSTRACT

A 4-amino-6-alkynyloxypyrimidine compound, which is represented by the formula (I) and has an effect of controlling a harmful organism, can be produced in a high yield by reacting a 4,6-difluoropyrimidine compound with an alkynol compound in an alkyl benzene in the presence of an organic salt and potassium carbonate and reacting the resulting compound with an amine compound without isolating the resulting compound.

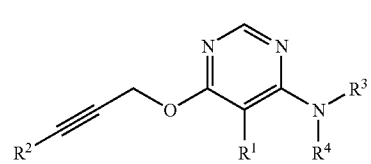

(I)

6 Claims, No Drawings

METHOD FOR PRODUCING PYRIMIDINE COMPOUND

TECHNICAL FIELD

The present invention relates to a novel method for producing a 4-amino-6-alkynyloxypyrimidine compound.

BACKGROUND ART

International Publication No. WO 2004/099160 describes that a 4-amino-6-alkynyloxypyrimidine compound has an excellent effect of controlling pests.

DISCLOSURE OF THE INVENTION

An object of the present invention is to provide an industrial production method capable of obtaining a 4-amino-6-alkynyloxypyrimidine compound having an effect of controlling pests in a high yield without performing isolation and complicated purification operations of an intermediate.

The present inventor have intensively studied so as to solve the above object and found an industrial production method capable of obtaining a 4-amino-6-alkynyloxypyrimidine compound represented by the following formula (I) in a high yield, and thus the present invention has been completed. That is, the present invention includes the following 1. to 10.

1. A method for producing a 4-amino-6-alkynyloxypyrimidine compound (I) represented by the formula (I):

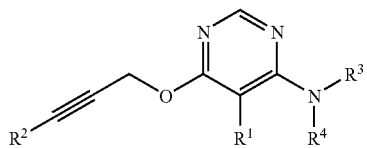

wherein $R^1$, $R^2$, $R^3$ and $R^4$ are as defined below, which comprises reacting a compound (II) represented by the formula (II):

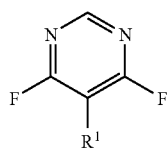

wherein $R^1$ represents a hydrogen atom or a halogen atom, with a compound (III) represented by the formula (III):

wherein $R^2$ represents a hydrogen atom or a methyl group, in the presence of an organic base and potassium carbonate, in an alkylbenzene to give a compound (IV) represented by the formula (IV):

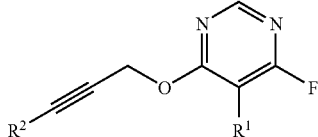

wherein $R^1$ and $R^2$ are as defined above, and the compound (IV) being without performing isolation and then reacting the resultant compound (IV) with a compound (V) represented by the formula (V) or a salt thereof:

wherein $R^3$ and $R^4$ are combined to form a C4-C7 polymethylene group, in which the C4-C7 polymethylene group may be substituted with one or more substituents selected from the group consisting of a halogen atom, a lower alkyl group substituted with halogen atom(s) and a lower alkyl group.

2. The producing method according to 1., wherein the organic base is triethylamine.
3. The producing method according to 1. or 2., wherein $R^1$ is fluorine.
4. The producing method according to any one of 1. to 3., wherein $R^2$ is a methyl group.
5. The producing method according to any one of 1. to 4., wherein the C4-C7 polymethylene group formed by combining $R^3$ and $R^4$ is a 2,4-dimethylpentamethylene group, that is, the compound of the formula (V) is 3,5-dimethylpiperidine.
6. The producing method according to any one of 1. to 5., wherein the alkylbenzene is toluene.
7. The producing method according to any one of 1. to 6., wherein an amount of the organic base is from 0.01 to 5 mol based on 1 mol of the compound represented by the formula (II).
8. The producing method according to any one of 1. to 6., wherein an amount of the organic base is from 0.05 to 0.5 mol based on 1 mol of the compound represented by the formula (II).
9. The producing method according to any one of 1. to 8., wherein a molar ratio of the organic base to potassium carbonate is organic base:potassium carbonate=1:2 to 1:30.
10. The producing method according to any one of 1. to 8., wherein a molar ratio of the organic base and potassium carbonate is organic base:potassium carbonate=1:4 to 1:25.

Proper examples and examples of various definitions included in the scope of the present invention in the above and following descriptions of the present description will be explained in detail below.

Unless otherwise specified, the term "lower" means a group having 1 to 6 or 2 to 6 carbon atoms, and preferably a group having 1 to 4 or 2 to 4 carbon atoms.

"One or more" may be from 1 to 6 as an appropriate example, and preferably from 1 to 4.

The "lower alkyl group" is preferably a straight or branched C1-C6 alkyl group and includes, for example, methyl, ethyl, n-propyl, isopropyl, n-butyl, isobutyl, sec-butyl, tert-butyl, n-pentyl, sec-pentyl, isopentyl, neopentyl, n-hexyl, and isohexyl.

The "halogen atom" includes a fluorine atom, a chlorine atom, a bromine atom, and an iodine atom, and is preferably a fluorine atom or a chlorine atom.

The "lower alkyl group substituted with halogen atom(s)" is preferably, for example, chloromethyl, difluoromethyl, trichloromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, or 6,6,6-trifluorohexyl, and particularly preferably trifluoromethyl.

The "alkylbenzene" is preferably, for example, toluene, xylene, or ethylbenzene, and particularly preferably toluene.

The "organic base" is preferably, for example, a tertiary amine compound, more preferably, for example, triethylamine, N,N-diisopropylethylamine, 1,8-diazabicyclo[5.4.0]undec-7-ene, or 1,5-diazabicyclo[4.3.0]non-5-ene, and particularly preferably triethylamine.

The C4-C7 polymethylene group (provided that the polymethylene group may be substituted with one or more substituents selected from the group consisting of a halogen atom, a lower alkyl group substituted with halogen atom(s) and a lower alkyl group) formed by combining $R^3$ and $R^4$ is preferably, for example, 2,4-dimethylpentamethylene.

Preferred examples of the salt in the present invention include acid addition salts such as inorganic acid addition salts (for example, hydrochloride salt, hydrobromide salt, sulfate, phosphate, and so on) and organic carboxylic acid sulfonic acid addition salts (for example, formate, acetate, trifluoroacetate, maleate, tartrate, fumarate, methanesulfonate, benzenesulfonate, toluenesulfonate, and so on).

The 4-amino-6-alkynyloxypyrimidine compound, in which the C4-C7 polymethylene group formed by combining $R^3$ and $R^4$ in the present invention is a 2,4-dimethylpentamethylene group, is represented by the following formula (Ia):

Formula (Ia)

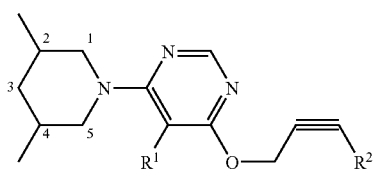

(Ia)

wherein $R^1$ and $R^2$ are as defined above.

Although isomers of the steric configuration and/or relative configuration exist according to the substituent on the ring in C4-C7 polymethylene formed by combining $R^3$ and $R^4$ in the present invention, the present invention includes both a single isomer and a mixture of one or more isomers in an optional mixing ratio.

The production method of the present invention will be described below.

(First Half Step)

A compound represented by the formula (IV) can be produced by reacting a compound represented by the formula (II) with a compound represented by the formula (III) in the presence of an organic base and potassium carbonate:

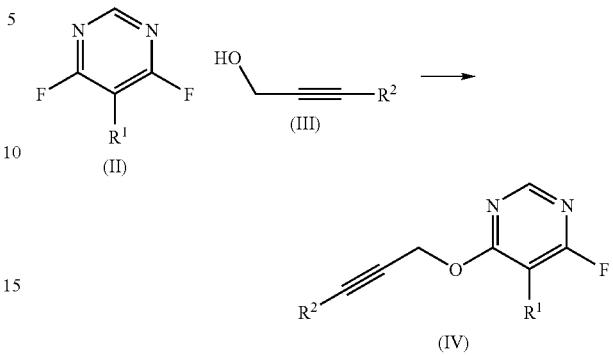

(wherein $R^1$ and $R^2$ are as defined above).

The reaction is carried out in an alkylbenzene solvent.

Examples of the alkylbenzene include toluene, xylene, and ethylbenzene.

The organic base used in the reaction includes, for example, a tertiary amine compound and specific examples thereof include triethylamine, N,N-diisopropylethylamine, 1,8-diazabicyclo[5.4.0]undec-7-ene, and 1,5-diazabicyclo[4.3.0]non-5-ene, and preferably triethylamine.

The amount of the organic base used in the reaction can appropriately vary depending on the conditions such as the kind of the solvent, kind of the organic base and reaction temperature. In view of the production cost and reaction yield, it is preferably from 0.01 to 5 mol, and more preferably from 0.05 to 0.5 mol, based on 1 mol of the compound represented by the formula (II).

The amount of the potassium carbonate used in the reaction can appropriately vary depending on the conditions such as the kind of the solvent, kind of the organic base and reaction temperature. In view of the production cost and reaction yield, it is preferably from 0.01 to 5 mol, and more preferably from 0.5 to 1.5 mol, based on 1 mol of the compound represented by the formula (II).

The molar ratio of the organic base and potassium carbonate used in the reaction can appropriately vary depending on the conditions such as the kind of the solvent, kind of the organic base and reaction temperature. In view of the production cost and reaction yield, it is preferably organic base: potassium carbonate=1:2 to 1:30, and more preferably organic base:potassium carbonate is from 1:4 to 1:25.

In view of the production cost and reaction yield, the amount of the compound represented by the formula (III) used in the reaction is preferably from 1 to 3 mol, and more preferably from 1 to 1.3 mol, based on 1 mol of the compound represented by the formula (II).

The reaction temperature of the reaction is appropriately decided depending on the conditions such as the solvent and organic base to be used, and is usually within a range from −20 to 150° C. or a boiling point temperature of the solvent, and preferably from 10 to 50° C.

The reaction time of the reaction is appropriately decided by confirming the progress of the reaction by way of high performance liquid chromatography (HPLC), gas chromatography, or thin layer chromatography, and is usually within a range from 0.1 to 48 hours, and preferably from 3 to 24 hours.

After completion of the reaction, a second half step can be started by the reaction with a compound represented by the formula (V) without performing isolation and purification operations. The remained amount of the unreacted raw compound represented by the formula (II) decreases by adding water before adding the compound represented by the formula (V) and, as a result, side reaction caused by the remained compound represented by the formula (II) can be suppressed in the second half step.

(Second Half Step)

The compound represented by the formula (I) can be produced by adding a compound represented by the formula (V) or a salt thereof to the reaction solution containing the compound represented by the formula (IV) produced in the first half step, followed by reaction:

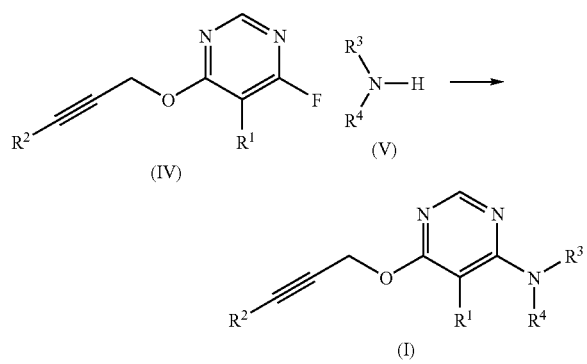

wherein $R^1$, $R^2$, $R^3$ and $R^4$ are as defined above.

The reaction is carried out in the presence of the solvent used in the first half step or a mixture of the solvent and water.

In view of the production cost and reaction yield, the amount of the compound represented by the formula (V) used in the reaction is preferably from 1 to 1.5 mol based on 1 mol of the compound represented by the formula (II).

The reaction temperature of the reaction is usually within a range from 0 to 60° C., and the reaction time is usually within a range from 1 to 48 hours.

In the second half step, usually, it is not necessary to add a base newly. However, when the unreacted raw material is remained, the reaction can be completed by adding potassium carbonate.

After completion of the reaction, the compound represented by the formula (I) can be isolated by washing the organic layer in the reaction mixture with water or diluted hydrochloric acid, followed by concentration.

The present invention will be described in more detail by way of Examples, Reference Formulation Examples and Test Example, but the present invention is not limited thereto.

EXAMPLE 1

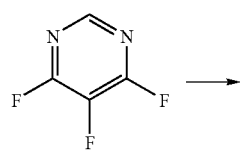

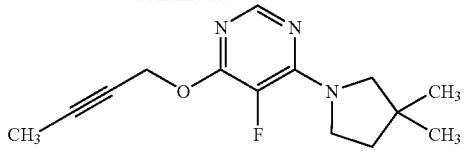

To a mixture obtained by adding 110.0 g of 4,5,6-trifluoropyrimidine, 114.6 g of potassium carbonate and 16.6 g of triethylamine to 220.0 g of toluene, 60.4 g of 2-butyn-1-ol is added dropwise at 25 to 30° C. over one hour, followed by stirring at 30° C. Then, 220.0 g of water is added dropwise into the reaction mixture, followed by stirring. Then, 85.4 g of 3,3-dimethylpyrrolidine is added dropwise and, after the mixture is stirred at 30° C., the reaction mixture is allowed to stand. After separating into the organic layer and the aqueous layer, the aqueous layer is removed and the organic layer is washed once with 220.0 g of 5% hydrochloric acid and then washed once with 220.0 g of water. The organic layer is concentrated to obtain 4-(2-butynyloxy)-5-fluoro-6-(3,3-dimethylpyrrolidin-1-yl)pyrimidine (hereinafter referred to as the present compound (1)).

EXAMPLE 2

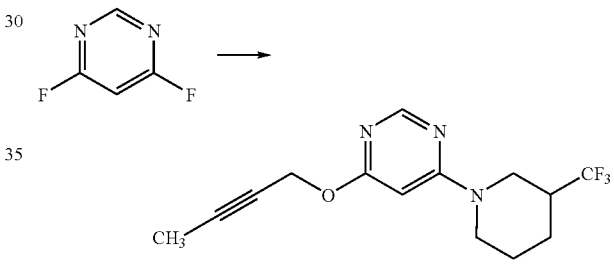

To a mixture obtained by adding 110.0 g of 4,6-difluoropyrimidine, 132.3 g of potassium carbonate and 19.2 g of triethylamine to 220.0 g of toluene, 69.8 g of 2-butyn-1-ol is added dropwise at 25 to 30° C. over one hour, followed by stirring at 30° C. Then, 220.0 g of water is added dropwise into the reaction mixture, followed by stirring. Then, 152.4 g of 3-trifluoromethylpyrrolidine is added dropwise and, after the mixture is stirred at 30° C., the reaction mixture is allowed to stand. After separating into the organic layer and the aqueous layer, the aqueous layer is removed and the organic layer is washed once with 220.0 g of 5% hydrochloric acid and then washed once with 220.0 g of water. The organic layer is concentrated to obtain 4-(2-butynyloxy)-6-(3-trifluoromethylpiperidino)pyrimidine (hereinafter referred to as the present compound (2)).

PRODUCTION EXAMPLE 3

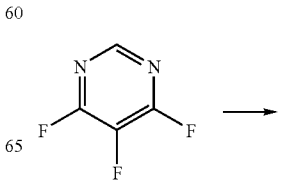

-continued

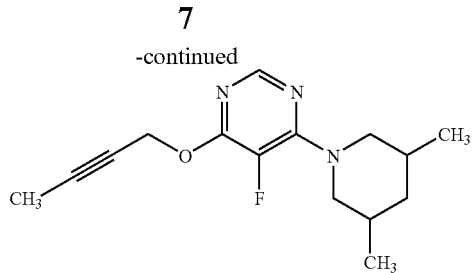

To a mixture obtained by adding 110.0 g of 4,5,6-trifluoropyrimidine, 114.6 g of potassium carbonate and 16.6 g of triethylamine to 220.0 g of toluene, 60.4 g of 2-butyn-1-ol was added dropwise at 25 to 30° C. over one hour, followed by stirring at 30° C. for 8 hours. Then, 220.0 g of water was added dropwise in the reaction mixture, followed by stirring for 14 hours. Then, 97.5 g of 3,5-dimethylpiperidine (a mixture of a cis-isomer and a trans-isomer in a mixing ratio of about 7:3) was added dropwise and, after the mixture was stirred at 30° C. for 6 hours, the reaction mixture was allowed to stand. After separating into the organic layer and the aqueous layer, the aqueous layer was removed and the organic layer was then washed once with 220.0 g of 5% hydrochloric acid and then washed once with 220.0 g of water. The organic layer was concentrated to obtain 213.8 g (yield: 94%) of 4-(2-butynyloxy)-5-fluoro-6-(3,5-dimethylpiperidino)pyrimidine (hereinafter referred to as the present compound (3)). Product purity 96% (HPLC)

PRODUCTION EXAMPLE 4

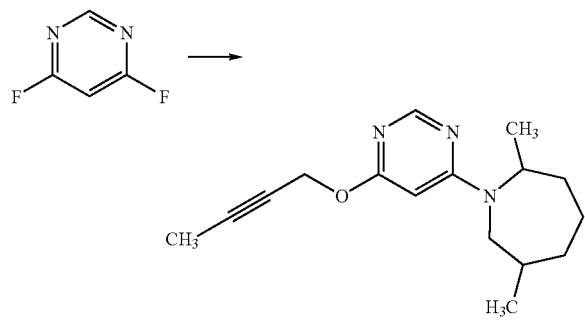

To a mixture obtained by adding 110.0 g of 4,6-difluoropyrimidine, 132.3 g of potassium carbonate and 19.2 g of triethylamine to 220.0 g of toluene, 69.8 g of 2-butyn-1-ol is added dropwise at 25 to 30° C. over one hour, followed by stirring at 30° C. Then, 220.0 g of water is added dropwise into the reaction mixture, followed by stirring. Then, 126.6 g of cis-2,6-dimethylhexahydroazepine is added dropwise and, after the mixture is stirred at 30° C., the reaction mixture is allowed to stand. After separating into the organic layer and the aqueous layer, the aqueous layer is removed and the organic layer is washed once with 220.0 g of 5% hydrochloric acid and then washed once with 220.0 g of water. The organic layer is concentrated to obtain 1-(6-(2-butynyloxy)pyrimidin-4-yl)-cis-2,6-dimethylhexahydroazepine (hereinafter referred to as the present compound (4)).

Reference Formulation Examples of the present compound will be explained. Parts are by weight.

REFERENCE FORMULATION EXAMPLE 1

Nine parts of each of the present compounds (1) to (4) is dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well mixing with stirring, to give an emulsifiable concentrate for each compound.

REFERENCE FORMULATION EXAMPLE 2

Nine parts of each of the present compounds (1) to (4) is added to a mixture of 4 parts of sodium lauryl sulfate, 4 parts of calcium lignin sulfonate, 20 parts of synthetic hydrated silicon oxide fine powder, and 65 parts of diatomaceous earth, followed well mixing with stirring, to give a wettable powder for each compound.

REFERENCE FORMULATION EXAMPLE 3

Three parts of each of the present compounds (1) to (4), 5 parts of synthetic hydrated silicon oxide fine powder, 5 parts of sodium dodecylbenzenesulfonate, 30 parts of bentonite, and 57 parts of clay are well mixed with stirring, and an appropriate amount of water is added to the mixture of these ingredients, followed by further stirring, granulation with a granulator, and drying by ventilation, to give a granule for each compound.

REFERENCE FORMULATION EXAMPLE 4

First, 4.5 parts of each of the present compounds (1) to (4), 1 part of synthetic hydrated silicon oxide fine powder, 1 part of Doriresu B (available from Sankyo Co., Ltd.) as a flocculent, and 7 parts of clay are well mixed in a mortar and then mixed with stirring in a juicer. To the resulting mixture is added 86.5 parts of cut clay, followed by well mixing with stirring, to give a dust for each compound.

REFERENCE FORMULATION EXAMPLE 5

Ten parts of each of the present compounds (1) to (4), 35 parts of white carbon containing 50 parts of polyoxyethylene alkyl ether sulfate ammonium salt, and 55 parts of water are mixed and pulverized by wet grinding method to give a formulation for each compound.

Test Example indicates that the present compound has an effect of controlling noxious organisms.
Tese Example
A formulation of a test compound obtained in Formulation Example 5 is diluted with water so that the active ingredient concentration comes to 500 ppm to prepare a test spray solution.

The seeds of cabbage are planted in polyethylene cups and grown until their first foliage leaves develop. The first foliage leaves are left and the other leaves are cut off. Some adults of silverleaf whiteflies are set free on the cabbage plants and allowed to lay eggs for about 24 hours. The cabbage plants with about 80 to 100 eggs thus laid are left in a greenhouse for 8 days, and the above test spray solution is sprayed at the rate of 20 ml/cup onto the cabbage plants with larvae being hatched from the laid eggs. On the 7th day after the application, the number of surviving larvae is counted.

As a result of this test, a sufficient control effect is confirmed in leaves of cabbage treated with each of test spray solutions of the present compounds (1) to (4).

INDUSTRIAL APPLICABILITY

The present invention is an industrial production method capable of obtaining a 4-amino-6-alkynyloxypyrimidine compound having an effect of controlling noxious pests in a high yield.

The invention claimed is:

1. A method for producing a 4-amino-6-alkynyloxypyrimidine compound (I) represented by the formula (I):

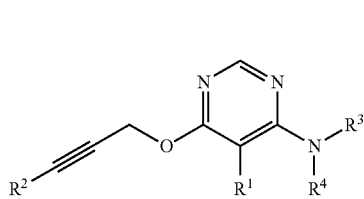
(I)

wherein $R^1$, $R^2$, $R^3$ and $R^4$ are as defined below, which comprises reacting a compound (II) represented by the formula (II):

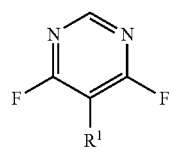
(II)

wherein $R^1$ represents a hydrogen atom or a halogen atom, with a compound (III) represented by the formula (III):

(III)

wherein $R^2$ represents a hydrogen atom or a methyl group, in the presence of an organic base and potassium carbonate, in an alkylbenzene to give a compound (IV) represented by the formula (IV):

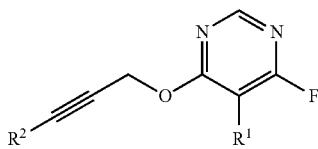
(IV)

wherein $R^1$ and $R^2$ are as defined above, and the compound (IV) being without performing isolation, and then reacting the resultant compound (IV) with a compound (V) represented by the formula (V) or a salt thereof:

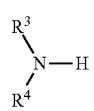
(V)

wherein $R^3$ and $R^4$ are combined to form a C4-C7 polymethylene group, in which the C4-C7 polymethylene group may be substituted with one or more substituents selected from the group consisting of a halogen atom, a lower alkyl group substituted with halogen atom(s) and a lower alkyl group.

2. The producing method according to claim 1, wherein the organic base is triethylamine.

3. The producing method according to claim 1, wherein $R^1$ is fluorine.

4. The producing method according to claim 1, wherein $R^2$ is a methyl group.

5. The producing method according to claim 1, wherein the C4-C7 polymethylene group formed by combining $R^3$ and $R^4$ is a 2,4-dimethylpentamethylene group, that is, the compound of the formula (V) is 3,5-dimethylpiperidine.

6. The producing method according to claim 1, wherein the alkylbenzene is toluene.

* * * * *